(12) United States Patent
Hee-Hanson et al.

(10) Patent No.: US 12,343,505 B1
(45) Date of Patent: Jul. 1, 2025

(54) MEDICAMENT DELIVERY DEVICE

(71) Applicant: Genzyme Corporation, Cambridge, MA (US)

(72) Inventors: Alexander Hee-Hanson, Melbourn (GB); Michael Parrott, Melbourn (GB)

(73) Assignee: Genzyme Corporation, Cambridge, MA (US)

(*) Notice: Subject to any disclaimer, the term of this patent is extended or adjusted under 35 U.S.C. 154(b) by 0 days.

(21) Appl. No.: 18/640,163

(22) Filed: Apr. 19, 2024

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31501* (2013.01); *A61M 5/3202* (2013.01); *A61M 2005/2073* (2013.01)

(58) Field of Classification Search
CPC ............ A61M 15/0081; A61M 5/2033; A61M 5/20; A61M 5/31501; A61M 5/31576; A61M 5/31565; A61M 2205/3553; A61M 2205/6027; A61M 2205/6045; A61M 2205/6054; A61M 2205/6063; A61M 2205/6009; A61M 2005/2073; A61M 2005/208; A61M 2205/581; A61M 2205/582; A61M 5/32; A61M 5/3202;
(Continued)

(56) References Cited

U.S. PATENT DOCUMENTS 2,522,961 A 9/1950 William
2,633,267 A 3/1953 Lebus
(Continued)

FOREIGN PATENT DOCUMENTS

DE 3921747 A1 1/1991
EP 3501577 A1 6/2019
(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.
U.S. Appl. No. 18/640,292, filed Apr. 19, 2024, Alexander Hee-Hanson.
U.S. Appl. No. 18/640,427, filed Apr. 19, 2024, Alexander Hee-Hanson.
(Continued)

Primary Examiner — Bradley J Osinski
(74) Attorney, Agent, or Firm — Fish & Richardson P.C.

(57) ABSTRACT

A medicament delivery device includes a needle being axially moveable from a retracted position to an exposed position. The device includes an actuation member configured to be movable to an actuation position to cause the needle to move from the retracted position to the exposed position. The device includes a locking member for preventing the movement of the actuation member to the actuation position, and a locking release member being axially moveable towards a proximal end of the medicament delivery device from a first position, in which the locking member is prevented from moving to a release position in which the actuation member is released for the movement of the actuation member to the actuation position, to a second position, in which the locking member is free to move to the release position in which the actuation member is released for the movement of the actuation member to the actuation position.

30 Claims, 8 Drawing Sheets

(58) Field of Classification Search
CPC .... A61M 5/3205; A61M 5/321; A61M 5/322; A61M 5/3221; A61M 2005/2006
USPC ........................................................ 604/506
See application file for complete search history.

(56) References Cited

U.S. PATENT DOCUMENTS

| | | | |
|---|---|---|---|
| 3,886,513 | A | 5/1975 | Smith et al. |
| 4,801,295 | A | 1/1989 | Spencer |
| 5,045,062 | A | 9/1991 | Henson |
| 5,176,275 | A | 1/1993 | Bowie |
| 5,328,484 | A | 7/1994 | Somers et al. |
| 5,396,051 | A | 3/1995 | Kuhn et al. |
| 5,478,316 | A | 12/1995 | Bitdinger et al. |
| 5,505,324 | A | 4/1996 | Danico |
| 5,505,706 | A | 4/1996 | Maus et al. |
| 5,536,917 | A | 7/1996 | Suppelsa et al. |
| 5,622,274 | A | 4/1997 | Bright |
| 5,738,658 | A | 4/1998 | Maus et al. |
| 5,984,899 | A * | 11/1999 | D'Alessio ........... A61M 5/3271 604/198 |
| 6,080,461 | A | 6/2000 | Wozniak et al. |
| 6,394,985 | B1 | 5/2002 | Lin |
| 7,762,981 | B2 | 7/2010 | Dacquay et al. |
| 7,887,506 | B1 | 2/2011 | Smolyarov et al. |
| 7,918,824 | B2 | 4/2011 | Bishop et al. |
| 8,133,198 | B2 | 3/2012 | Neer |
| 8,409,138 | B2 | 4/2013 | James et al. |
| 8,734,394 | B2 | 5/2014 | Adams et al. |
| 9,044,553 | B2 | 6/2015 | James et al. |
| 9,402,957 | B2 | 8/2016 | Adams et al. |
| 9,872,961 | B2 | 1/2018 | Fourt et al. |
| 10,118,001 | B2 | 11/2018 | Fourt et al. |
| 10,314,981 | B2 | 6/2019 | Sampson et al. |
| 10,350,362 | B2 | 7/2019 | Dennis, Jr. et al. |
| 10,363,377 | B2 | 7/2019 | Atterbury et al. |
| 11,298,462 | B2 | 4/2022 | Atterbury et al. |
| 11,331,432 | B2 | 5/2022 | Holmqvist et al. |
| 11,369,751 | B2 | 6/2022 | Ruan et al. |
| 11,452,821 | B2 | 9/2022 | LaFever et al. |
| 2002/0055712 | A1 | 5/2002 | Neracher |
| 2004/0039336 | A1 | 2/2004 | Amark et al. |
| 2005/0101919 | A1* | 5/2005 | Brunnberg ............ A61M 5/326 604/197 |
| 2005/0273061 | A1 | 12/2005 | Hommann et al. |
| 2006/0224124 | A1 | 10/2006 | Scherer |
| 2007/0270777 | A1 | 11/2007 | Dacquay et al. |
| 2008/0097311 | A1 | 4/2008 | Dacquay et al. |
| 2008/0097390 | A1 | 4/2008 | Dacquay et al. |
| 2008/0269692 | A1 | 10/2008 | James et al. |
| 2009/0036868 | A1 | 2/2009 | Pinedjian et al. |
| 2009/0281496 | A1 | 11/2009 | Matusch |
| 2010/0211005 | A1 | 8/2010 | Edwards et al. |
| 2011/0054414 | A1 | 3/2011 | Shang et al. |
| 2011/0144594 | A1 | 6/2011 | Sund et al. |
| 2011/0202011 | A1 | 8/2011 | Wozencroft |
| 2011/0319813 | A1 | 12/2011 | Kamen et al. |
| 2013/0237921 | A1 | 9/2013 | Lannan et al. |
| 2013/0267897 | A1 | 10/2013 | Kemp et al. |
| 2014/0236076 | A1 | 8/2014 | Marshall et al. |
| 2014/0249483 | A1 | 9/2014 | Kiilerich et al. |
| 2014/0263156 | A1 | 9/2014 | Newsom et al. |
| 2014/0276637 | A1 | 9/2014 | Massey, Jr. |
| 2015/0246180 | A1 | 9/2015 | Fenlon et al. |
| 2015/0273162 | A1 | 10/2015 | Holmqvist |
| 2016/0001015 | A1 | 1/2016 | Kucuk et al. |
| 2016/0354555 | A1 | 12/2016 | Gibson et al. |
| 2016/0367763 | A1 | 12/2016 | Tschirren et al. |
| 2017/0215699 | A1 | 8/2017 | Ouyang et al. |
| 2017/0216526 | A1 | 8/2017 | Brereton et al. |
| 2017/0224929 | A1 | 8/2017 | Sampson et al. |
| 2017/0246403 | A1 | 8/2017 | Cowe et al. |
| 2017/0361034 | A1 | 12/2017 | Scheller et al. |
| 2018/0250471 | A1 | 9/2018 | Grimoldby et al. |
| 2018/0339114 | A1 | 11/2018 | Wendland et al. |
| 2019/0030249 | A1 | 1/2019 | Gonzalez et al. |
| 2019/0192785 | A1 | 6/2019 | Wendland et al. |
| 2019/0366000 | A1* | 12/2019 | Cowe .................. A61M 5/2422 |
| 2020/0114041 | A1 | 4/2020 | Alas et al. |
| 2020/0316314 | A1 | 10/2020 | Buri et al. |
| 2021/0077732 | A1 | 3/2021 | Egelhofer |
| 2021/0196900 | A1 | 7/2021 | Apply et al. |
| 2022/0015429 | A1 | 1/2022 | Brown et al. |
| 2022/0176042 | A1* | 6/2022 | Belisle ................ A61M 5/3204 |
| 2022/0395640 | A1 | 12/2022 | Schwartzentruber |
| 2023/0001099 | A1 | 1/2023 | Dunn |
| 2023/0238105 | A1 | 7/2023 | Schneider et al. |
| 2023/0347074 | A1 | 11/2023 | Gavin |
| 2024/0009397 | A1 | 1/2024 | In et al. |

FOREIGN PATENT DOCUMENTS

| | | |
|---|---|---|
| WO | WO 2002/047746 A1 | 6/2002 |
| WO | WO 2011/109205 A2 | 9/2011 |
| WO | WO 2016/081238 A1 | 5/2016 |
| WO | WO 2019/074788 A1 | 4/2019 |
| WO | WO 2020/190529 A1 | 9/2020 |

OTHER PUBLICATIONS

U.S. Appl. No. 18/640,600, filed Apr. 19, 2024, Alexander Hee-Hanson.

U.S. Appl. No. 18/640,710, filed Apr. 19, 2024, Alexander Hee-Hanson.

* cited by examiner

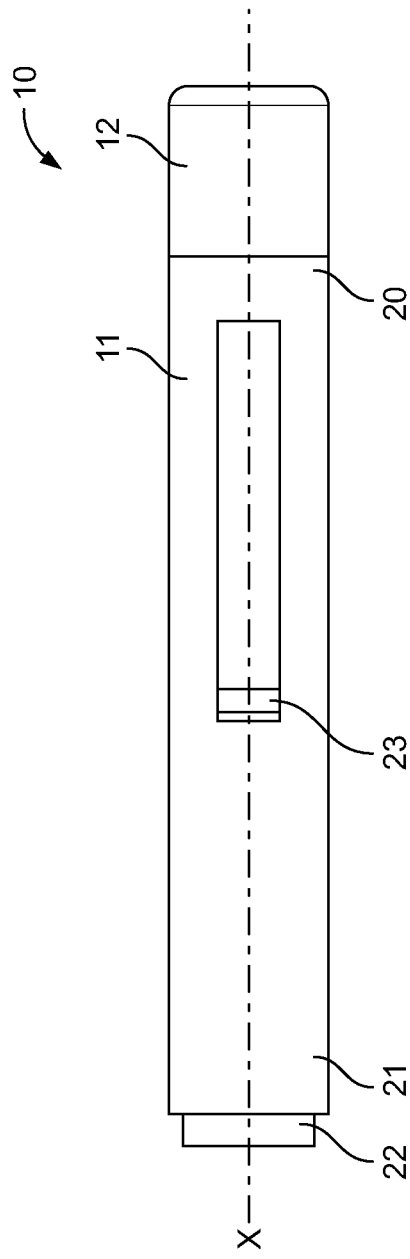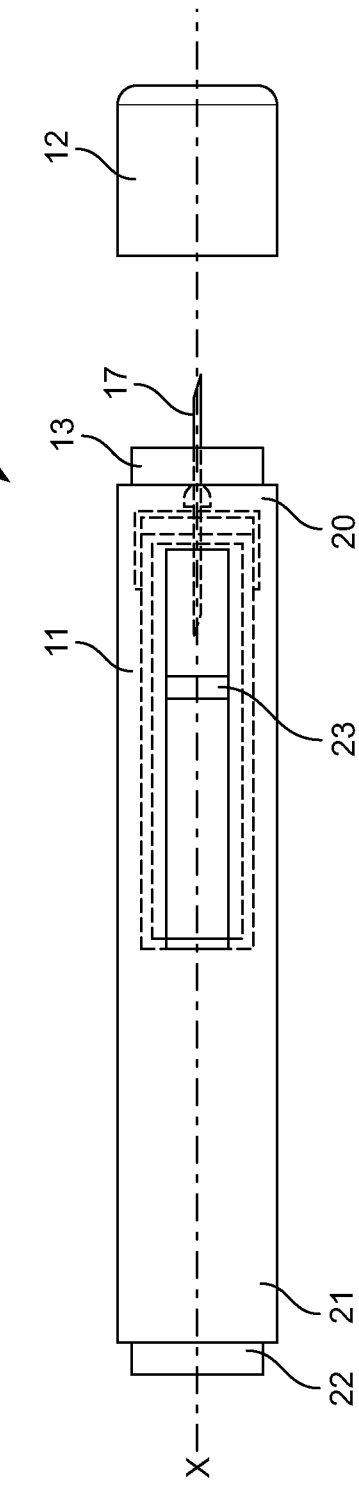
FIG. 1A
FIG. 1B

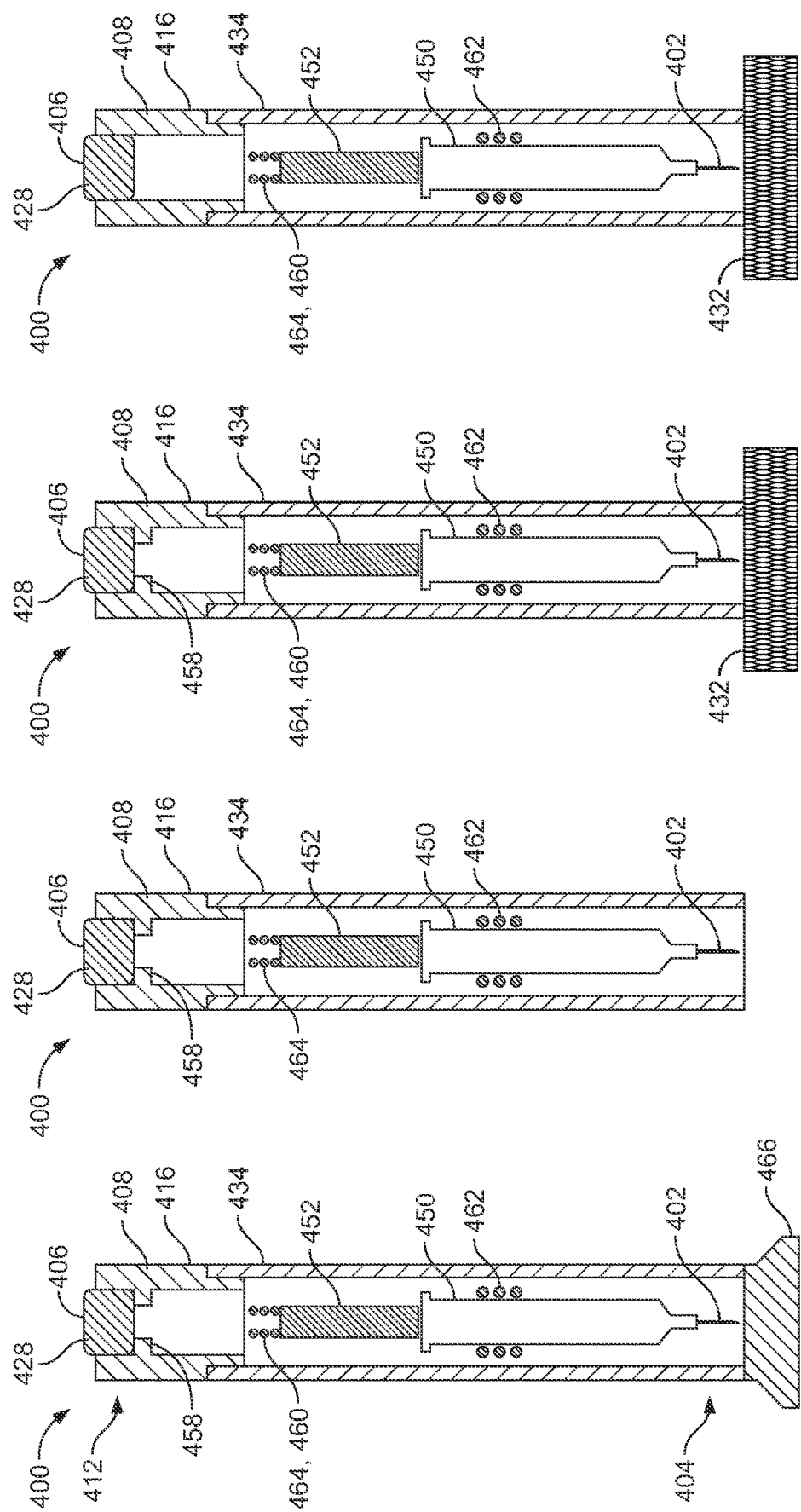

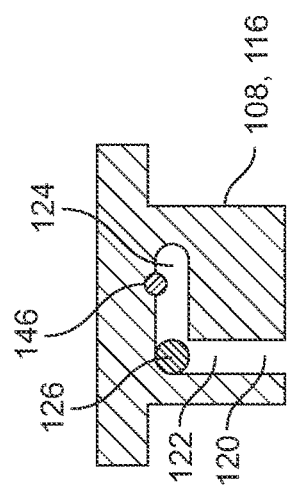
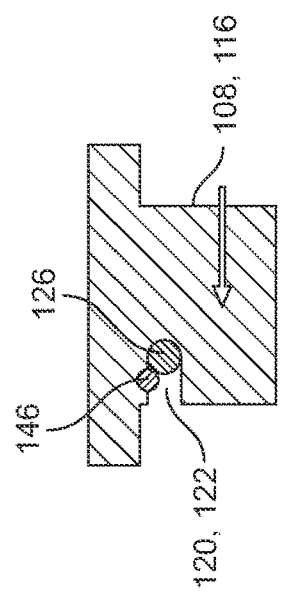
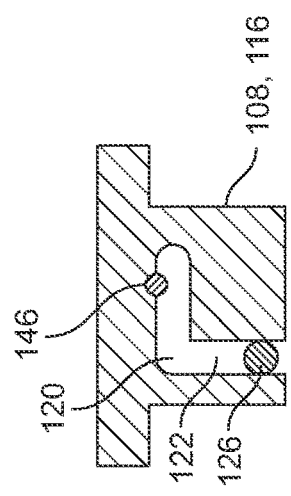
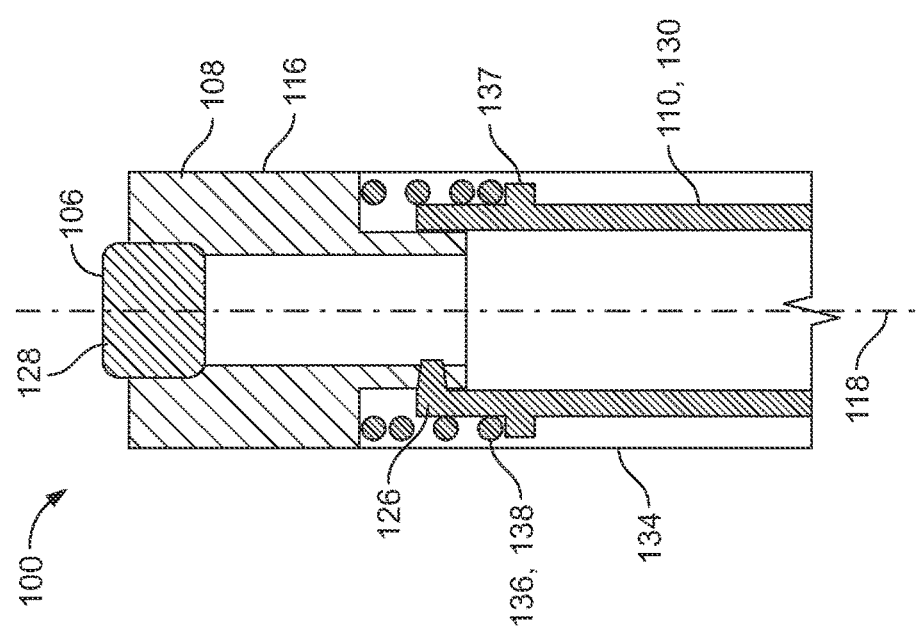

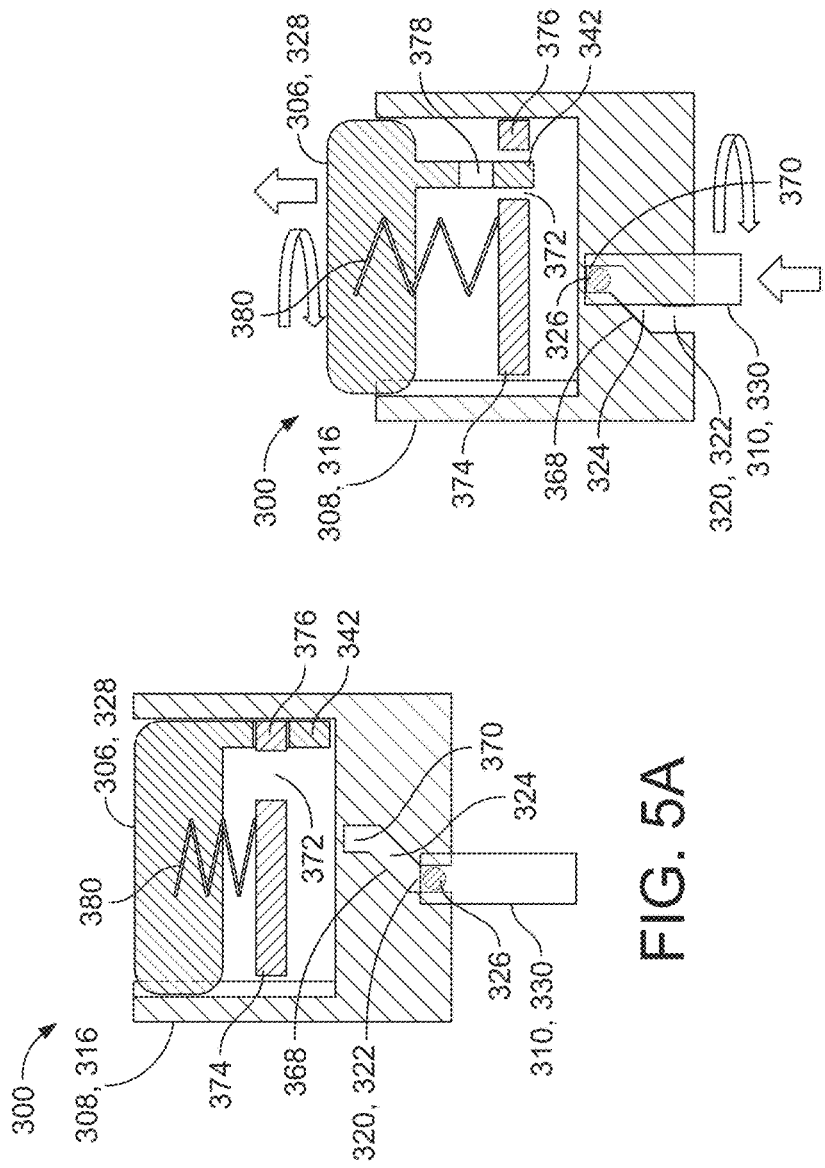

MEDICAMENT DELIVERY DEVICE

TECHNICAL FIELD

The present disclosure relates to a medicament delivery device and to a method of using a medicament delivery device.

BACKGROUND

Medicament delivery devices, such as auto-injectors, are known in the art for dispensing medicament to an injection site of a patient. In some cases, an actuation member is able to be depressed irrespective of whether the device has been placed at an injection site. Depressing the actuation member independently of the device being placed at an injection site can cause the needle to be unintentionally exposed for stick injuries and can cause a dose of medicament to be unintentionally dispensed. This can also lead to a waste of medicament which may be costly.

SUMMARY

According to a first aspect, a medicament delivery device includes:
 a needle for injecting medicament into a user, the needle arranged at a distal end of the medicament delivery device, the needle being axially moveable from a retracted position in which the needle is retracted within the medicament delivery device to an exposed position in which the needle is exposed from a distal end of the medicament delivery device for injecting medicament into a user;
 an actuation member configured to be moveable by a user to an actuation position to cause the needle to move from the retracted position to the exposed position;
 a locking member for preventing movement of the actuation member to the actuation position, the locking member being configured to move from a locking position, in which the actuation member is prevented from moving to the actuation position, to an actuation member release position in which the actuation member is released for movement to the actuation position; and
 a locking member release configured to axially extend from the distal end of the medicament delivery device, the locking member release being axially moveable towards a proximal end of the medicament delivery device from a first position, in which the locking member is prevented from moving to the actuation member release position, to a second position, in which the locking member is free to move to the actuation member release position.

In some embodiments, the locking member release is configured to be axially moveable from the first position to the second position as the locking member release is depressed against an injection site.

In some embodiments, the second position corresponds to a fully-depressed position of the locking member release.

In some embodiments, the locking member is configured to be moveable by a user from the locking position to the actuation member release position when the locking member release is in the second position. In some embodiments, the locking member is configured to not be moveable by a user from the locking position to the actuation member release position when the locking member release is in the first position.

In some embodiments, the locking member is configured such that movement of the locking member release to the second position causes the locking member to move to the actuation member release position.

In some embodiments, the medicament delivery device further comprises a bias, such as a spring, configured to bias the locking member into the actuation member release position. In some embodiments, the medicament delivery device further comprises a bias, such as a spring, configured to bias the locking member out of the actuation member release position. In some embodiments, the medicament delivery device further comprises a bias, such as a spring, configured to bias the locking member into the locking position.

In some embodiments, the actuation member is arranged at the proximal end of the medicament delivery device.

In some embodiments, the actuation member comprises a button which is depressible by a user to the actuation position.

In some embodiments, the locking member is rotatable from the locking position to the actuation member release position.

In some embodiments, the locking member comprises a lock ring. In some embodiments, the lock ring is arranged substantially coaxial with a longitudinal axis of the medicament delivery device. In some embodiments, the lock ring is rotatable about the longitudinal axis of the medicament delivery device from the locking position to the actuation member release position. In some embodiments, the actuation member is arranged such that the lock ring extends circumferentially around the actuation member.

In some embodiments, the locking member release comprises an axially moveable sleeve beyond which the needle is configured to extend when the needle is in the exposed position and when the locking member release is in the second position.

In some embodiments, the actuation member is rotationally coupled to the locking member.

In some embodiments, the medicament delivery device comprises an axial guide arrangement configured to guide axial movement of the locking member release with respect to the locking member while limiting or restricting, or substantially preventing, rotational movement of the locking member release with respect to the locking member.

In some embodiments, the locking member release is configured to be received within a body of the medicament delivery device in the second position of the locking member release.

In some embodiments, the medicament delivery device comprises a bias (such as a compression spring) configured to bias the locking member release into the first position.

In some embodiments, one of the locking member and locking member release comprises a slot having an axially extending portion and a circumferentially extending portion angled with respect to the axially extending portion and wherein the other of the locking member and locking member release comprises a guide slidably received within the slot so as to be slidable along and between the axially extending portion and the circumferentially extending portion. In some embodiments, the axially extending portion leads directly to the circumferentially extending portion.

In some embodiments, the guide is configured to slide along the axially extending portion of the slot as the locking member release moves to the second position. In some embodiments, the guide is configured to slide along the axially extending portion of the slot as the locking member release is depressed by a user against an injection site.

In some embodiments, the axially extending portion is configured to prevent movement of the locking member from the locking position to the actuation member release position.

In some embodiments, the circumferentially extending portion of the slot is angled (e.g. with respect to a longitudinal axis of the medicament delivery device), so as to be substantially perpendicular to the axially extending portion, optionally such that movement of the guide along the circumferentially extending portion of the slot does not cause the locking member release and the locking member to move axially with respect to each other upon rotation of the locking member, e.g. about a longitudinal axis of the device. In some embodiments, the circumferentially extending portion is configured to correspond with a fully depressed position of the locking member release.

In some embodiments, the slot comprises one or more detents or projections configured to provide a haptic or audible indication to the user upon engagement of the one or more detects or projections with the guide. In some embodiments, the one or more detents or projections are arranged within the slot so as to correspond to a fully depressed position of the locking member release or so as to correspond to the locking member being in the actuation member release position.

In some embodiments, the circumferentially extending portion of the slot is angled (e.g. with respect to a longitudinal axis of the medicament delivery device) such that axial movement of the locking member release with respect to the locking member causes the locking member to move (e.g. rotate) from the locking position to the actuation member release position.

In some embodiments, the circumferentially extending portion and the axially extending portion of the slot together define a L-shape.

In some embodiments, the axially extending portion of the slot is a first axially extending portion and wherein the slot comprises a second axially extending portion after the circumferentially extending portion, e.g. so as to prevent rotation of the locking member release with respect to the locking member after the locking member has been moved into the actuation member release position and/or after the guide has moved into the second axially extending portion.

In some embodiments, one of the locking member or actuation member comprises an aperture, such as a slot or recess, configured to (e.g. rotationally) align with and receive a blocking member (e.g. an axially extending projection) of the other of the locking member or actuation member when the locking member is in the actuation member release position so as to allow the actuation member to move to the actuation position, the aperture being (e.g. rotationally) misaligned with the blocking member when the locking member is not in the actuation member release position (e.g. when the locking member is in the locking position) so as to prevent the actuation member from moving to the actuation member release position. In some embodiments, rotation of the locking member to the actuation member release position causes the recess to align with the blocking member.

In some embodiments, the actuation member is configured to be held in a depressed position (e.g. in which the actuation member is flush or sub-flush (or recessed) with a distal end of a body of the medicament delivery device) when the locking member release is in the first position or when the locking member is in the locking position.

In some embodiments, one of the locking member and the actuation member comprises a latch configured to engage with a complementary latching feature provided on the other of the locking member and the actuation member for holding the actuation member in the depressed position when the locking member release is in the first position or when the locking member is in the locking position.

In some embodiments, the actuation member is configured to move to a raised position when the locking member is moved from the locking position to the actuation member release position.

In some embodiments, the medicament delivery device comprises a bis configured to bias the actuation member into the raised position.

In some embodiments, the actuation member is configured such that when the actuation member is in the raised position, the actuation member is moveable (e.g. depressible) by a user to the actuation position.

In some embodiments, the actuation member comprises a button depressible by a user.

In some embodiments, movement of the actuation member to the actuation position causes or triggers the movement of the needle from the retracted position to the exposed position and/or causes medicament contained within a container (e.g. a syringe or a cartridge of the device) to be dispensed through the needle.

In some embodiments, the medicament delivery device further comprises a container (e.g. a syringe or a cartridge) of medicament.

According to a second aspect, a method of using a medicament delivery device includes:
   moving a locking member release of the medicament delivery device axially towards a proximal end of the medicament delivery device from a first position, in which a locking member of the medicament delivery device is prevented from moving to an actuation member release position, to a second position, in which the locking member is free to move to the actuation member release position;
   moving the locking member from a locked position, in which an actuation member of the medicament delivery device is prevented from moving to an actuation position, to an actuation member release position in which the actuation member is released for movement to the actuation position; and
   moving the actuation member to the actuation position to cause a needle for injecting medicament into a user, the needle being arranged at a distal end of the medicament delivery device, to move axially from a retracted position, in which the needle is retracted within the medicament delivery device, to an exposed position, in which the needle is exposed from the distal end of the medicament delivery device for injecting medicament into a user.

According to a third aspect, a method of using a medicament delivery device includes:
   moving a locking member release of the medicament delivery device axially towards a proximal end of the medicament delivery device from a first position, in which a locking member of the medicament delivery device is prevented from moving to an actuation member release position, to a second position, in which the locking member is free to move to the actuation member release position;
   wherein moving the locking member release to the actuation member release position causes the locking member to move from a locked position, in which an actuation member of the medicament delivery device is prevented from moving to an actuation position, to an actuation member release position in which the actuation member is released for movement to the actuation position; and moving the actuation member to the actuation position to cause a needle for injecting medicament into a user, the needle being arranged at a distal end of the medicament delivery device, to move axially from a retracted position, in which the needle is retracted within the medicament delivery device, to an exposed position, in which the needle is exposed from the distal end of the medicament delivery device for injecting medicament into a user.

According to a fourth aspect, a medicament delivery device includes a needle for injecting a medicament, the needle arranged at a distal end of the medicament delivery device, the needle being axially movable from a proximal position in which the needle is retracted within the medicament delivery device to a distal position in which a distal end of the needle extends from a distal end of the medicament delivery device for injecting the medicament.

In some embodiments, the medicament delivery device includes an actuation member configured to be movable to an actuation position to cause the needle to move from the proximal position to the distal position.

In some embodiments, the medicament delivery device includes a locking member for preventing the actuation member from moving to the actuation position, the locking member being configured to move from (i) a locking position in which the actuation member is prevented from moving to the actuation position to (ii) a release position in which movement of the actuation member to the actuation position is allowed.

In some embodiments, the medicament delivery device includes a locking release member configured to axially extend from the distal end of the medicament delivery device, the locking release member being axially movable towards a proximal end of the medicament delivery device from (i) a first position in which the locking member is prevented from moving to the release position to (ii) a second position in which movement of the locking member to the release position is allowed.

In some embodiments, the locking member is configured to be movable from the locking position to the release position when the locking release member is in the second position.

In some embodiments, the medicament delivery device is configured such that movement of the locking release member to the second position causes the locking member to move to the release position.

In some embodiments, the medicament delivery device is configured such that relative movement between a guide element and a slot causes the locking member to move from the locking position to the release position as the locking release member moves from the first position to the second position, the slot being angled relative to a longitudinal axis of the medicament delivery device.

In some embodiments, the medicament delivery device includes a bias element configured to bias the locking member to the release position. In some cases, the bias element includes a spring.

In some embodiments, the locking member includes a lock ring.

In some embodiments, the medicament delivery device includes an axial guide configured to guide axial movement of the locking release member with respect to the locking member while limiting, restricting, or substantially preventing rotational movement of the locking release member with respect to the locking member.

In some embodiments, one of the locking member and the locking release member includes a slot having an axially extending portion and a circumferentially extending portion angled with respect to the axially extending portion. In some cases, the other of the locking member and the locking release member includes a guide element configured to be slidably received within the slot so as to be slidable along and between the axially extending portion and the circumferentially extending portion.

In some embodiments, the guide element includes a protrusion.

In some embodiments, the guide element is configured to slide along the axially extending portion of the slot as the locking release member moves to the second position.

In some embodiments, the axially extending portion is configured to limit movement of the locking member from the locking position to the release position.

In some embodiments, the axially extending portion is configured to limit rotational movement of the locking member from the locking position to the release position.

In some embodiments, the circumferentially extending portion of the slot is angled to be substantially perpendicular to the axially extending portion.

In some embodiments, the slot includes one or more detents or projections configured to provide a haptic or audible indication upon engagement of the one or more detents or projections with the guide element.

In some embodiments, the circumferentially extending portion of the slot is angled such that axial movement of the locking release member with respect to the locking member causes the locking member to move from the locking position to the release position.

In some embodiments, the axially extending portion is configured to limit movement of the locking member from the locking position to the release position, the circumferentially extending portion of the slot is angled to be substantially perpendicular to the axially extending portion and the slot includes one or more detents or projections configured to provide a haptic or audible indication upon engagement of the one or more detects or projections with the guide element.

In some embodiments, the axially extending portion is configured to limit movement of the locking member from the locking position to the release position, the circumferentially extending portion of the slot is angled such that axial movement of the locking release member with respect to the locking member causes the locking member to move from the locking position to the release position, and the slot includes one or more detents or projections configured to provide a haptic or audible indication upon engagement of the one or more detects or projections with the guide element.

In some embodiments, one of the locking member or the actuation member includes an aperture configured to align with and receive a blocking member of the other of the locking member or actuation member when the locking member is in the release position. In some cases, the medicament delivery device is configured such that when the blocking member is aligned with the aperture, the actuation member is allowed to move to the actuation position.

In some embodiments, when the locking member is not in the release position, movement of the actuation member to the release position is limited.

In some embodiments, the aperture is defined by a slot or a recess.

In some embodiments, the actuation member is configured to be held in a depressed position when the locking release member is in the first position.

In some embodiments, the actuation member is configured to be held in a depressed position when the locking member is in the locking position.

According to a fifth aspect, a medicament delivery device includes a housing and a needle arranged at a distal end of the housing. The needle being axially movable between (i) a proximal needle position in which the needle is within the medicament delivery device and (ii) a distal needle position in which a distal end of the needle extends from a distal end of the housing.

In some embodiments, the medicament delivery device includes a first member configured to be movable relative to the housing from a first first member position to a second first member position such that moving the first member to the second first member position causes the needle to move from the proximal needle position to the distal needle position.

In some embodiments, the medicament delivery device includes a second member configured to limit movement of the first member from the first first member position to the second first member position, the second member being configured to move from (i) a first second member position in which movement of the first member to the second first member position is limited to (ii) a second second member position in which movement of the first member to the second first member position is allowed.

In some embodiments, the medicament delivery device includes a third member configured to extend from the distal end of the housing, the third member being axially movable in a proximal direction relative to the housing from (i) a first third member position in which movement of the second member to the second position is limited to (ii) a second third member position in which movement of the second member to the second second member position is allowed.

According to a sixth aspect, a medicament delivery device includes a housing and a first member configured to be movable relative to the housing from a first first member position to a second first member position to cause a medicament to be dispensed from the medicament delivery device.

In some embodiments, the medicament delivery device includes a second member configured to move from (i) a first second member position in which movement of the first member to the second first member position is limited to (ii) a second second member position in which movement of the first member to the second first member position is allowed.

In some embodiments, the medicament delivery device includes a third member configured to move in a proximal direction relative to the housing from (i) a distal position in which movement of the second member to the second second member position is limited to (ii) a proximal position in which movement of the second member to the second second member position is allowed.

In some embodiments, the movement of the second member from the first second member position to the second second member position includes a rotation relative to the housing.

According to a seventh aspect, a method includes:
moving a locking release member of a medicament delivery device axially towards a proximal end of the medicament delivery device from (i) a first position in which movement of a locking member of the medicament delivery device to a release position is limited to (ii) a second position in which movement of the locking member to the release position is allowed;

moving the locking member from (i) a locked position in which movement of an actuation member of the medicament delivery device to an actuation position is limited to (ii) a release position in which the actuation member is movement to the actuation position is allowed; and moving the actuation member to the actuation position to cause a needle for injecting medicament to move axially from (i) a proximal position in which the needle is retracted within a distal end of the medicament delivery device to (ii) a distal position in which a distal end of the needle extends from the distal end of the medicament delivery device for injecting medicament.

In some embodiments, the method includes injecting the medicament through the needle and into a patient.

These and other aspects will be apparent from and elucidated with reference to the embodiments described hereinafter.

BRIEF DESCRIPTION OF THE DRAWINGS

Embodiments will now be described, by way of example, with reference to the accompanying drawings, in which:

FIG. 1A is a schematic view of a medicament delivery device with a cap attached;

FIG. 1B is a schematic view of the medicament delivery device of FIG. 1A with the cap removed;

FIG. 2A is a schematic view of a medicament delivery device prior to use (i.e. in a pre-use configuration);

FIG. 2B is a schematic view of the device of FIG. 2A with the cap removed;

FIG. 2C is a schematic view of the device of FIG. 2A showing the device placed at an injection site;

FIG. 2D is a schematic view of the device of FIG. 2A with a lock ring of the device having been rotated to allow a button of the device to be depressed by a user;

FIG. 3A is a schematic view of parts of a medicament delivery device according to a first embodiment;

FIG. 3B is a schematic view of a locking member of the embodiment of FIG. 3A, showing a guide arranged within an axially extending portion of a slot provided in the locking member;

FIG. 3C is a schematic view of the first embodiment showing the guide arranged within a circumferentially extending portion of the slot after a locking member release of the device has been moved to a second position by depressing the locking member release against an injection site;

FIG. 3D is a schematic view of the first embodiment showing the locking member having been rotated so as to cause the guide to slide along the circumferentially extending portion of the slot;

FIG. 5A is a schematic view of parts of a device according to a third, showing the actuation member being held in a depressed position in which it lies flush with or recessed within the locking member;

FIG. 5B is a schematic view of the device of FIG. 5A showing the actuation member being released from a latch and biased into a raised position for being depressed by a user; and FIG. 5C is a schematic view of the device of FIG. 5A showing the actuation member being depressed by a user against an injection site in order to cause the needle to move from a retracted position to an exposed position for delivering a dose of medicament.

DETAILED DESCRIPTION

Figure 2G:
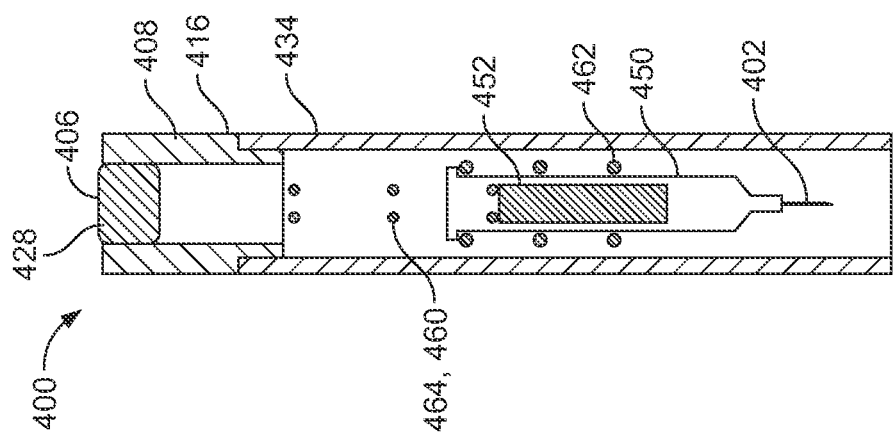
FIG. 2G is a schematic view of the device of FIG. 2A showing the device removed from the injection site after the needle has retracted within the device after delivery of the dose.

A drug delivery device, as described herein, may be configured to inject a medicament into a patient. For example, delivery could be sub-cutaneous, intra-muscular, or intravenous. Such a device could be operated by a patient or a care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process.

Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIGS. 2A to 2G show the sequential steps of operating a medicament injection device 400.

As shown in FIG. 2A, the device 400 comprises a body 434, a syringe 450 having a needle 402 and an axially moveable plunger 452 for dispensing medicament from the syringe 450. The device comprises a cap 466 which is removably attached to the device 400 and covers a distal end 404 of the body 434 so as to prevent stick injuries.

As shown in FIGS. 2B-2C, in order to deliver a dose of medicament to an injection site 432, the cap 466 is removed (FIG. 2B) and the device is placed at the injection site 432 (FIG. 2C). An actuation member 406 in the form of a button 428 is prevented from being depressed by a locking member 408 in the form of a lock ring 416 which is rotatable by a user about a longitudinal axis of the device, by a radially-projecting stop 458. The stop 458 may be provided in the locking member 408 or the stop 458 may be provided on a separate part of the device. In FIG. 2D, in order to allow the button 428 to be depressed by a user, the lock ring 416 is rotated about the longitudinal axis of the device to an actuation member release position (or button release position) in which the stop 458 no longer prevents the button 428 from being depressed by a user.

Figure 2F:
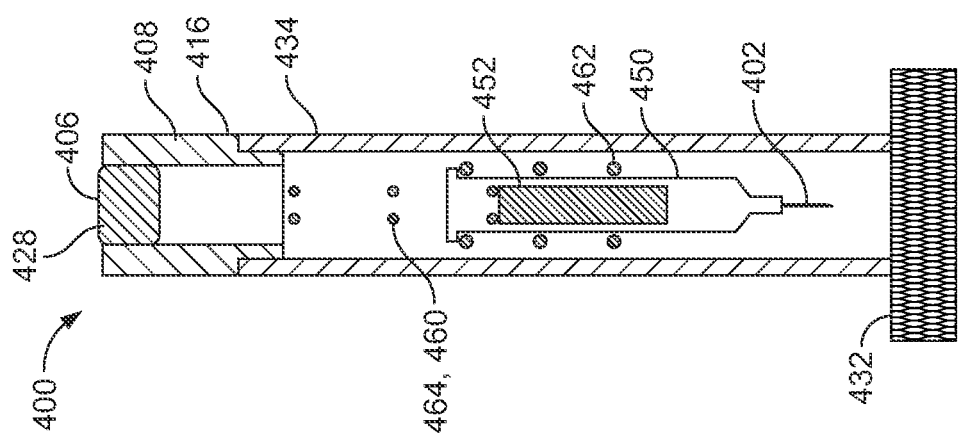
FIG. 2F is a schematic view of the device of FIG. 2A showing the needle having retracted within the device after a dose has been delivered.
Figure 2E:
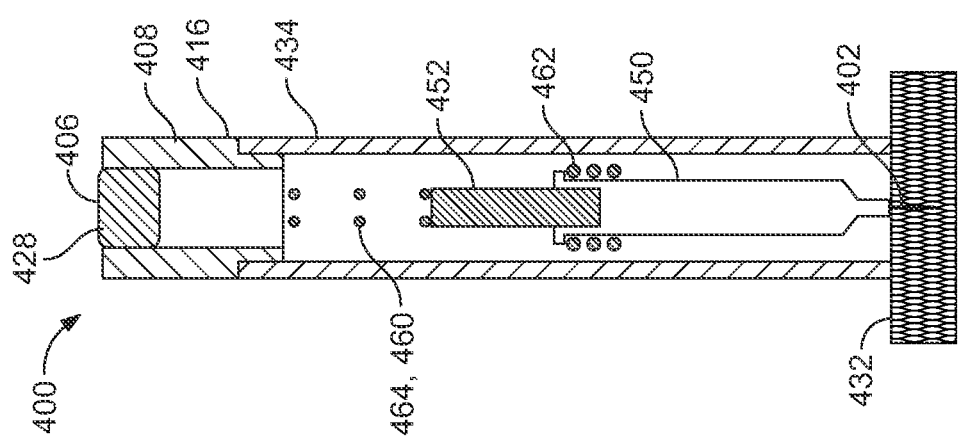
FIG. 2E is a schematic view of the device of FIG. 2A after the button has been depressed and the needle has been caused to move to an exposed position.

Turning now to FIG. 2E, the user then depresses the button 428 to actuate or trigger a needle mechanism so as to release the syringe 450 for distal axial movement towards the injection site 432 such that the needle 402 moves from a pre-use retracted position to an exposed (or "uncovered") position for delivering medicament to the injection site 432. The syringe 450 is moved distally so as to move the needle 402 thereof to the exposed position under a biasing force provided by a bias 464 in the form of a compression spring 460. Depressing the button 428 also releases the plunger 452 which, biased by the bias 464, moves along the syringe 450 towards the distal end 404 of the device 400 to force medicament within the syringe 450 through the needle 402, thereby delivering a dose of medicament. Thus, the bias 464 causes both the syringe 450 to move distally so as to move the needle 402 thereof to the exposed position and also causes the plunger 452 to move within the syringe 450 so at to cause a dose of medicament within the syringe 450 to be dispensed through the needle 402. As shown in FIG. 2F, once the dose has been delivered, a medicament container bias 462, embodied by a further spring 462, then causes the needle 402 to move axially back to the retracted position, away from the injection site 432 in a proximal direction. As shown in FIG. 2G, the device 400 is then removed from the injection site 432 for later reuse or for disposal.

Turning now to FIGS. 3A-3G, a first embodiment of medicament delivery device 100 is shown. For ease of illustration, parts of the medicament delivery device 100 are shown, but it will be appreciated that the device 100 of the first and all other embodiments disclosed hereinbelow may be provided with the other parts of the device 400 discussed with reference to FIGS. 2A-2G and in certain embodiments, the device 100 can be considered a modification of the device 400. For example, the device 100 of the first embodiment may comprise the needle mechanism (including bias 452 and medicament container bias 462) of the device 400 of FIG. 2A to 2G or parts thereof.

Similar to the device 400, the device 100 of the first embodiment comprises a needle for injecting medicament into a user (or to an injection site). The needle is arranged at a distal end 109 of the device 100 in a similar fashion to that of the device of FIGS. 2A-2G. The needle is axially moveable from a retracted position in which the needle is retracted within the medicament delivery device 100 (e.g within a body 134 of the device 100) and an exposed position in which the needle is exposed from a distal end of the medicament delivery device (e.g. from a distal end of the body 134) for injecting medicament into a user (or to an injection site).

The device comprises an actuation member 106 which in this embodiment is arranged at a proximal end 112 of the device 100, although the actuation member 106 may be provided elsewhere in other envisaged embodiments. The actuation member 106 is configured to be moveable by a user to an actuation position to cause a needle of the device 100 to move from the retracted position to the exposed position. For example, the actuation member 106 may be configured to actuate a needle mechanism configured to move the needle from the retracted position to the exposed position or it may act directly on the needle or medicament container to cause the needle to move from the retracted position to the exposed position. In this embodiment, the actuation member 106 is embodied as a button 128 which is depressible by a user to the actuation position, although any suitable actuation member 106 may instead be used.

The device further comprises a locking member 108 configured to move from a locking position, in which the actuation member 106 is prevented from being moved to the actuation position (e.g. the button 128 is prevented from being depressed by a user), to an actuation member release position in which the actuation member is released for movement to the actuation position (e.g. for being depressed by a user). Thus, the locking member 108 is configured to lock the actuation member 106 in a first position to prevent the actuation member 106 from moving to the actuation position. In some embodiments, a locking member bias, such as a spring, may be provided which is configured to bias the locking member 108 into the actuation member release position. In other embodiments, the locking member bias may instead be configured to bias the locking member 108 into its locking position.

In some embodiments, the locking member 108 may be provided as an annular lock ring 116. The lock ring 116 is arranged substantially coaxial with a longitudinal axis 118 of the medicament delivery device 100 and the lock ring 116 is rotatable about the longitudinal axis 118 of the device 100 from the locking position to the actuation member release position.

In the first and all other embodiments disclosed hereinbelow, the actuation member 106 is arranged such that the lock ring 116 extends circumferentially around the actuation member 106 such that the actuation member 106 is arranged within and slidably received within the annulus of the annular lock ring 116, although this is not essential. The actuation member 106 is also rotationally coupled to the locking member 108 in the first embodiment, although this is also not essential and in other embodiments the actuation member 106 may be rotationally decoupled from the locking member 108.

Figure 3G:
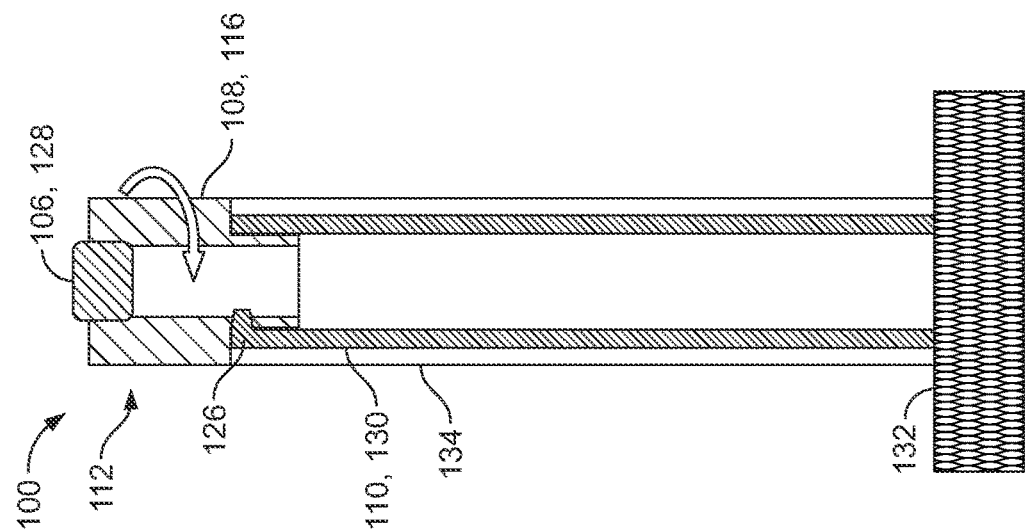
FIG. 3G is a schematic view of the device of FIG. 3A showing the locking member being free to rotate, for example so that a user may rotate it, to an actuation member release position, after the device has been depressed against the injection site.
Figure 3F:
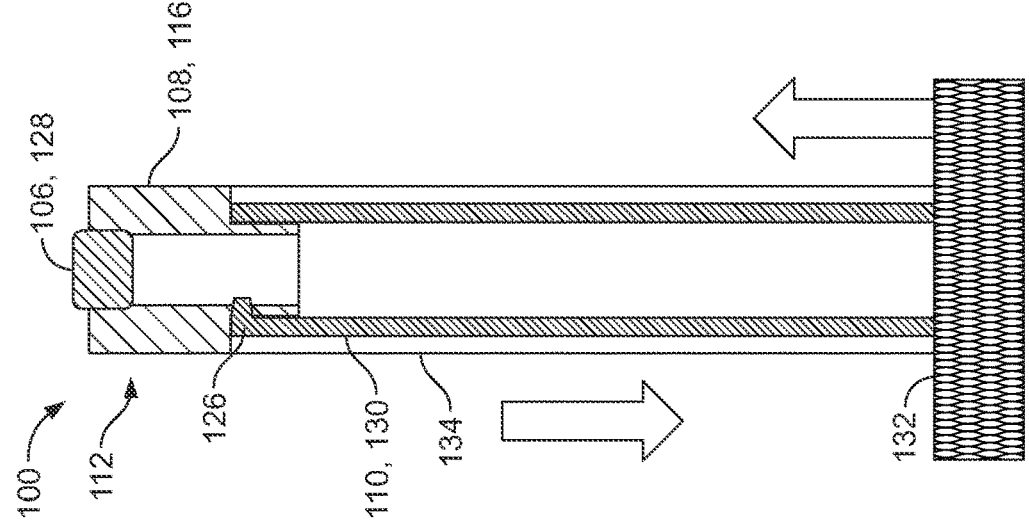
FIG. 3F is a schematic view of the device of FIG. 3E wherein a locking member release has been moved proximally by a user pressing the device against an injection site.
Figure 3E:
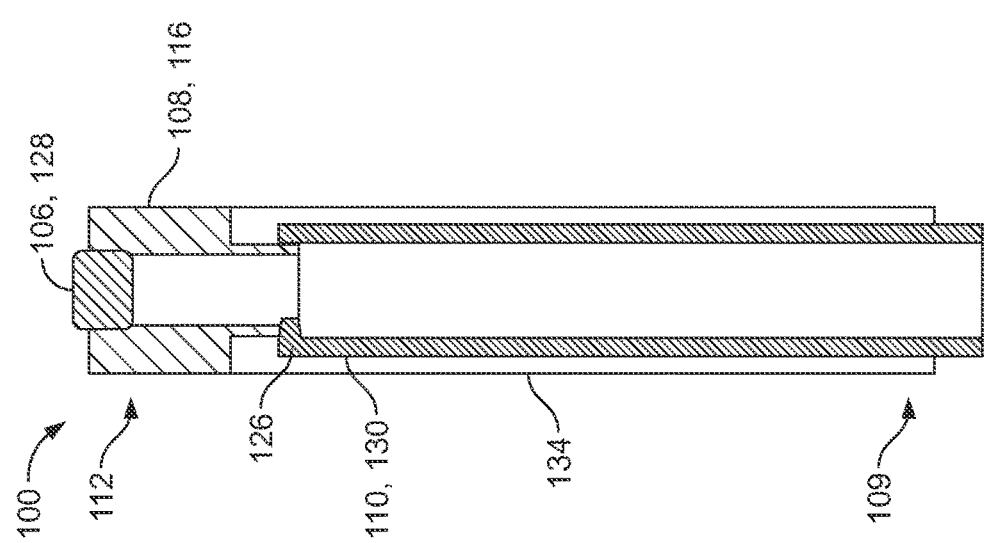
FIG. 3E is a schematic view of the device of the first embodiment in an initial configuration, prior to use, wherein certain parts are omitted for ease of illustration.

As shown in FIG. 3E, a locking member release 110 (or locking release member) is configured to axially extend from the distal end 109 of the medicament delivery device 100 prior to the device 100 being provided at the injection site 132 (i.e. in a pre-use configuration of the device) and prior to the actuation member 106 being moved to the actuation position. The locking member release 110 is axially moveable towards the proximal end 112 of the device 100 from a first position, in which the locking member 108 is prevented from moving to the actuation member release position, to a second position, in which the locking member 108 is free to move to the actuation member release position.

In this embodiment, the locking member release 110 comprises an axially moveable sleeve 130 (or "collar") which is substantially coaxial with the longitudinal axis 118 of the device 100. The locking member release 110 is also slidably received within a body 134 of the device although this is not essential. Prior to the device 100 being provided at the injection site 132, the sleeve 130 extends from the distal end 109 of the device 100 but placement of the device 100 against the injection site 132 causes the sleeve 130 to move axially in a proximal direction under a depression force applied by the user to a retracted position in which the sleeve 130 is retracted within the body 134 device and in which the sleeve 130 may lie flush or recessed within a distal end of the body 134 of the device 100. In this retracted position of the locking member release 110 (i.e. when the locking member release 110 is in the second position), the needle may be configured to extend axially beyond the locking member release 110 when the needle is in the exposed position for delivering a dose of medicament.

In some embodiments, a locking member release bias 136 may be provided which is configured to bias the locking member release 110 (e.g. sleeve 130) into the first position, i.e. in an axially distal direction. In some embodiments, the locking member release bias 136 may be provided as a compression spring 138 which may in some embodiments be arranged substantially coaxially with the longitudinal axis 118 of the device 100 and in some embodiments may extend around the locking member release 110 as shown in FIG. 3A for example. In some embodiments, the locking member release bias 138 may be arranged between the locking member 108 and the locking member release 110 so as to bias the locking member release 110 axially away from the locking member 108, for example the locking member release bias 136 may be configured to engage a surface of the locking member 108 and a radially extending projection or shoulder 137 provided on the locking member release 110. In other embodiments, the locking member release bias 136 may be configured to engage a surface of the locking member 108 or body 134 and a proximal end surface of the locking member release 110 or sleeve 130.

The locking member 108 comprises a slot 120 (FIGS. 3B-D) comprising an axially extending portion 122 and a circumferentially extending portion 124 angled with respect to the axially extending portion 122. The axially extending portion 122 leads directly to the circumferentially extending portion 124, although embodiments having an intermediate portion of the slot 120 are also envisaged. The locking member release 110 comprises a guide 126, embodied as a pin 126, which is slidably received within the slot 120 so as to be slidable along and between the axially extending portion 122 and the circumferentially extending portion 124 as the locking member release 108 is depressed against the injection site. It will be appreciated that in other embodiments, the locking member release 110 may instead comprise the slot 120 and the locking member 108 may comprise the guide 126.

The axially extending portion 122 prevents movement of the locking member 108 from the locking position to the actuation member release position by preventing rotation of the locking member 108 with respect to the locking member release 110 when the guide 126 is received within the axially extending portion 122. Thus, the axially extending portion 122 prevents movement of the locking member 108 from the locking position to the actuation member release position until the locking member release 110 has been depressed sufficiently such that the guide 126 enters the circumferentially extending portion 124.

The circumferentially extending portion 124 allows movement of the locking member 108 from the locking position to the actuation member release position by allowing rotation of the locking member 108 about the longitudinal axis 118 of the device 100 with respect to the locking member release 110 when the guide 126 is received within the circumferentially extending portion 124. In this embodiment, the circumferentially extending portion 124 is arranged substantially perpendicular to the axially extending portion 122 (such that the axially extending portion 122 and the circumferentially extending portion 124 together define a L-shape) such that movement of the guide 126 along the circumferentially extending portion 124 does not cause the locking member release 110 and the locking member 108 to move axially with respect to each other. In other embodiments, such as those described hereinbelow the circumferentially extending portion 124 may be angled substantially less than perpendicularly with respect to the axially extending portion 122 so as to define a ramped surface 268 (see FIG. 4D) so as to cause rotation of the locking member 108 as the locking member release 110 moves axially upon engagement of the guide 126 with the ramped surface 268.

In the embodiment of FIGS. 3A-3G, the circumferentially extending portion 124 corresponds to a fully depressed position of the locking member release 110 in which, for example, the locking member release 110 may lie flush or recessed within the distal end 104 of the body 134. The circumferentially extending portion 122 being arranged substantially perpendicular to the axially entering portion 124 advantageously supports the force provided by the locking member release bias 136 such that the holding force is reduced to zero when the guide 126 is arranged within the circumferentially extending portion when the locking member release 110 is fully depressed.

In some embodiments the device 100 may further comprise an axial guide arrangement configured to guide axial movement of the locking member release 110 with respect to the locking member 108 or body 134 while limiting or restricting, or substantially preventing, rotational movement of the locking member release 110 with respect to the locking member 108 or body 134. For example, the axial guide arrangement may comprise an axially extending rail provided on the body 134 and the locking member release 110 may comprise a guide configured to be slidable along the rail such that the locking member release 110 may slide from its extended position to its retracted or depressed position while substantially or entirely preventing rotation of the locking member release 110 with respect to the body 134. It will be appreciated that in some embodiments, the locking member release 110 may instead comprise the rail and the body 134 may instead comprise the guide.

The operation of the device 100 of the first embodiment will now be described with reference to FIGS. 3E-3G. In an initial, pre-use configuration of the device 100, shown in FIG. 3E, the needle is in its retracted position within the housing 134 and the locking member release 110 extends axially from the distal end 102 of the device 100. In this configuration, the guide 126 is slidably received within the axially extending portion 112 of the slot 120 thereby preventing rotation of the locking member 108 from its locking position to its needle actuation position such that the actuation member 106 (button 128) is unable to be moved (e.g. depressed) such that the needle is not able to move from its retracted position to its exposed position.

Next, as shown in FIG. 3F, the user places the device 100 at the injection site 132 and presses the locking member release 110 against the injection site 132 so as to cause the locking member release 110 to slide axially towards a proximal end 112 of the device 110. This causes the guide 126 to slide along the axially extending portion 122 of the slot 120 provided in the locking member 108 until, when the locking member release 110 is in its fully depressed position, the guide 126 enters the circumferentially extending portion 124 of the slot 120, thereby allowing the locking member 108 to be freely rotated about the longitudinal axis 118 of the device 100 from its locking position to its actuation member release position, for example by a user or by a locking member bias.

As shown in FIG. 3G, the locking member 108 is then rotated (either by a user or by a locking member bias) to the actuation member release position such that the stop 458 (see FIGS. 2A-G) and actuation member 106 (button 128) are moved with respect to each other so as to remove the blocking engagement between the actuation member 106 (button 128) and the stop 458 (see FIG. 2A) which, in the initial configuration, prevented the actuation member 106 (button 128) from being depressed. Thus, the actuation member 106 (button 128) is now able to be depressed by the user so as to cause the actuation member 106 (button 128) to move to the actuation position to cause the needle to move from its retracted position to its exposed position. In some embodiments, the device may comprise the needle mechanism of FIGS. 2A-2G such that moving the actuation member 106 (button 128) to the actuation position causes the needle mechanism to be trigged, thereby causing the syringe 450 to first be released and to move towards the injection site 432 under a biasing force provided by the bias 452 so as to cause the needle to move from its retraced position to its exposed position and, subsequently or simultaneously, causing the plunger 452 to move within the syringe 450 under action of the biasing force provided by the bias 452 so as to dispense a dose of medicament through needle 402. In other embodiments, the needle mechanism may be configured such that the actuation member 106 acts directly on the medicament cartridge 450, causing the needle to move from the retracted position to the exposed position upon the actuation member 406 being moved to the actuation position and the bias 452 biases the plunger 452 to move within the syringe 450. In other embodiments, the needle mechanism may be omitted entirely and the actuation member 106 may act directly on the medicament cartridge 450 and the plunger 452 so as to cause their respective movements.

In some examples, the operation from here is the same as that shown in FIGS. 2F-2G. For example, after the dose has been delivered, the syringe 450 (or cartridge or container) is caused to move proximally away from the injection site 132, thereby causing the needle to move back to its retracted position such that the needle is no longer exposed from the distal end 109 of the device 100. The user then removes the device 100 from the injection site for later use or for disposal.

Turning now to FIGS. 4A to 4F, a device 200 according to a second embodiment is shown. The device 200 of the second embodiment is substantially the same as the device 100 of the first embodiment and, as such, redundant discussion between the two embodiments is omitted for the sake of conciseness. Corresponding features shared between the first and second embodiments share corresponding reference numerals, with those of the second embodiment being increased by 100 as compared to those of the first embodiment.

Figure 4A:
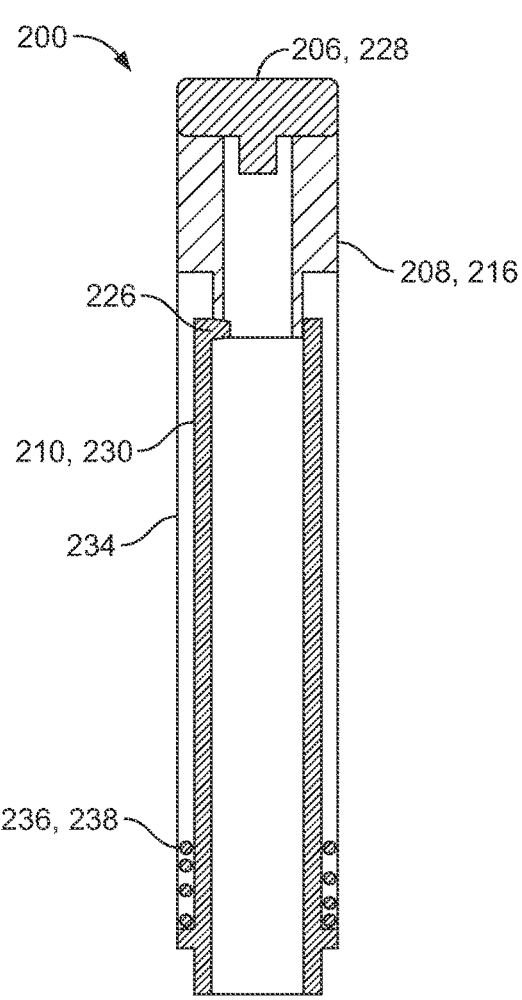
FIG. 4A is a schematic view of parts of a device according to a second embodiment, showing the device in an initial configuration, prior to use, wherein certain parts are omitted for ease of illustration.
Figure 4C:
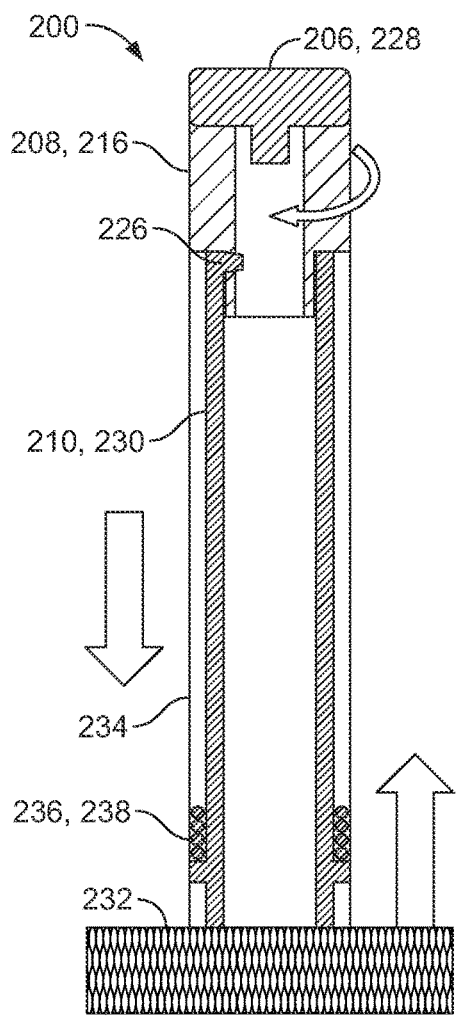
FIGS. 4C and 4D are schematic views of the device of FIG. 4A, showing the locking member release pressed against an injection site by the user, causing the guide to move along a circumferentially extending portion of the slot, the circumferentially extending portion being angled so as to cause rotation of the locking member from a locking position to an actuation member release position and showing the locking member release being fully depressed such that the guide is received within a further axially extending position so as to prevent further rotation of the locking member.
Figure 4B:
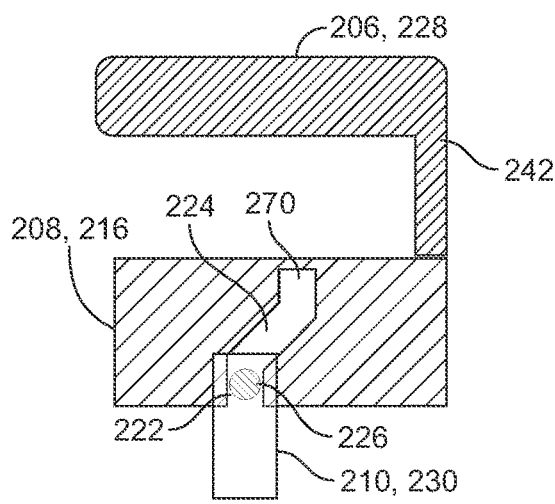
FIG. 4B is a schematic view of the device of FIG. 4A showing a locking member and showing a guide arranged within an axially extending portion of a slot provided within the locking member when the device is in the initial, pre-use configuration.

In the same way as in the first embodiment, the device 200 of the second embodiment comprises a locking member release 210, also provided as a collar or sleeve 230, which is slidably received within a body 234 from an extended position to a depressed or retracted position. In the depressed or retracted position, the locking member release 210 may in some embodiments lie flush (as shown in FIG. 4C) or recessed within a distal end of the body 234. As is also the case with the first embodiment, the locking member release 210 is substantially tubular defining an annulus which is substantially co-linear with the longitudinal axis 218 of the device 200, although, as with the first embodiment, any suitable shape may instead be used.

The device 200 of the second embodiment differs from the first with respect to the configuration of the locking member 208 (e.g., lock ring 216) and the actuation member 206. In some examples, this is the only difference and as such, aside from the differences described hereinbelow, the above discussion in respect of the first embodiment can apply equally to the second embodiment.

Figure 4D:
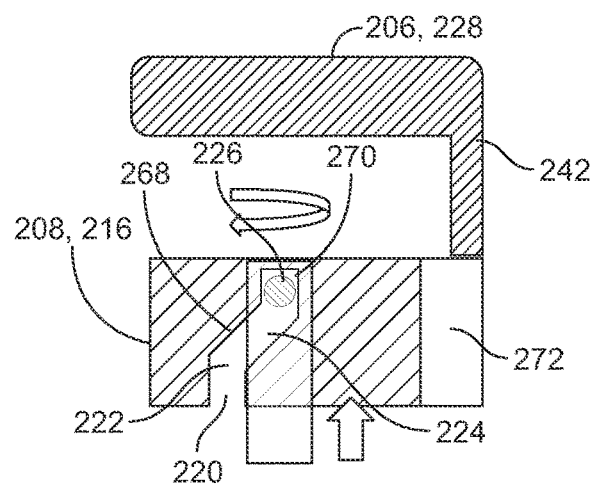
Figure 4E:
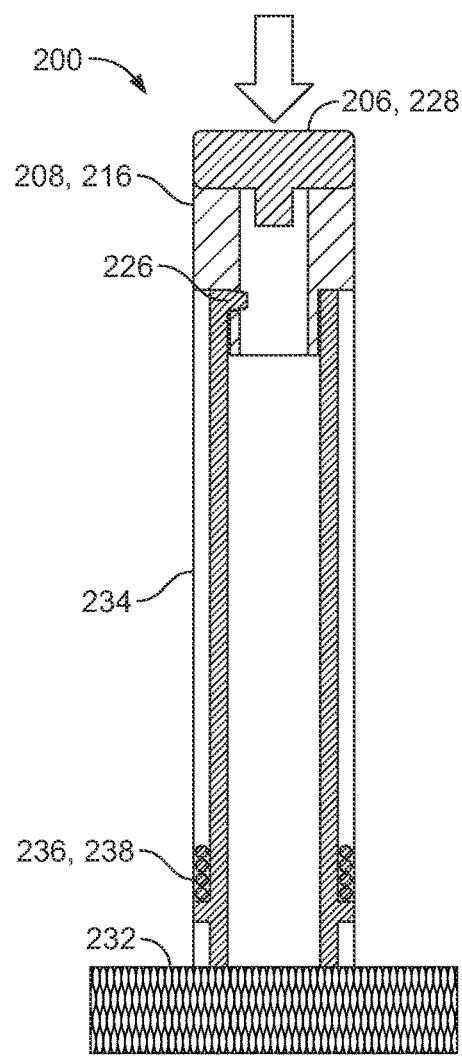
FIGS. 4E and 4F are schematic views of the device of FIG. 4A showing the actuation member being moved to an actuation position by the user.
Figure 4F:
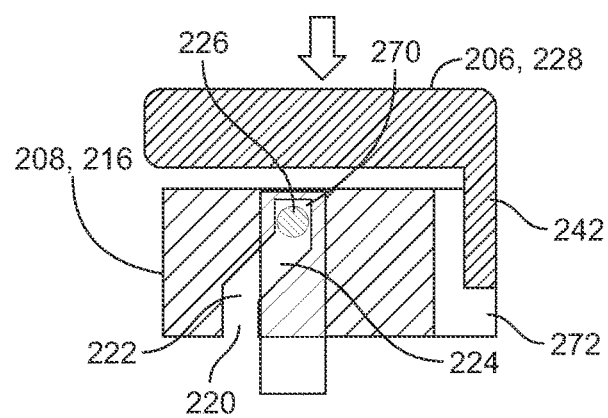

While in the first embodiment the circumferentially extending portion 124 of the slot 120 is substantially perpendicular to the axially extending portion 122 such that the locking member release 110 releases the locking member 108 such that the locking member 108 is free for rotation by a user to the actuation member release position when the locking member release 110 is moved to its second position but the axial movement of the locking member 108 does not itself cause rotation of the locking member release 110, in the second embodiment, the circumferentially extending portion 222 is angled substantially less than 90 degrees (for example between 5, 10, 20, 30, 45, 50, 60, 70, 80, or 85 degrees or between a range defined by any two of these values) so as to define a ramped surface 268 (FIG. 4D). The ramped surface 268 extends simultaneously in both a circumferential and an axial direction and the guide 226 is configured to move along the ramped surface 268 such that movement of the locking member release 210 to its second position (e.g. while the locking member 210 is being depressed so as to move axially towards a proximal end of the device 200) causes the guide 226 to move along the ramped surface 268. The angle of the ramped surface 268 imparts a rotational force component on the locking member 208 so as to cause the locking member 208 to rotate with respect to the locking member release 210 (and in some embodiments thereby also with respect to the body 234 which in some embodiments is rotationally coupled to the locking member release, for example by way of an axial guide arrangement such as that described with respect to the first embodiment). This rotation of the locking member 208 causes the locking member 208 to move from its locking position towards its actuation member release position in which the actuation member 206 is released for movement to its actuation position (e.g. the actuation member 206 is released to be depressed by a user). Further proximal axial movement of the locking member release 210 to its fully-depressed position causes the guide 226 to then enter a second axially extending portion 270 of the slot 220, thereby once more rotationally coupling or locking the locking member 208 to the locking member release 210 and thereby preventing the locking member 208 from being rotated out of its actuation member release position. In embodiments which do not comprise the second axially extending portion 270 of the slot 220, the ramped surface 268 may reduce, but not entirely eliminate, the holding force required to overcome the force provided by the locking member release bias 236.

In this embodiment, in the initial (or pre-use) configuration, prior to rotation of the locking member 208 by proximal axial movement of the locking member release 210, the actuation member 206 is prevented from being moved to its actuation position (i.e. button 228 is prevented from being depressed) by the blocking engagement of a blocking member 242 (in this embodiment provided as an axially extending finger 242) of the actuation member 206 with a stop which in this embodiment is provided as a surface of the locking member 208. In other embodiments the stop may be fixed with respect to a body of the device 200. Rotation of the locking member 208, caused by movement of the locking member release 210 to its second (fully-depressed) position, to its actuation member release position causes the blocking member 242 to axially align with an aperture (or slot) 272 provided in the locking member 208, thereby removing the blocking engagement of the blocking member 242 with the locking member 208 and allowing the blocking member 242 to slide axially within the aperture 272 when the actuation member 206 is moved to its actuation position (i.e. when the actuation member is depressed by a user). Other embodiments are envisaged wherein the locking member 208 instead comprises the blocking member 242 and wherein the actuation member 206 instead comprises the aperture 272.

In some examples, the only other difference between the first and second embodiments is that the locking member release bias 236 (spring 236) is biased against the body 234 rather than the locking member 208, although this aspect is interchangeable with the first embodiment and vice versa.

Turning now to FIGS. 5A-C, parts of a device 300 according to a third embodiment are shown. The device 300 of the third embodiment is substantially the same as the device 200 of the second embodiment and, as such, redundant discussion between the two embodiments is omitted for the sake of conciseness. Corresponding features shared between the second and third embodiments share corresponding reference numerals, with those of the third embodiment being increased by 100 as compared to those of the second embodiment.

The device 300 of the third embodiment differs from the second with respect to the configuration of the locking member 308 (e.g., lock ring 316) and the actuation member 306 (e.g., button 328) and by the provision of an actuation member support 374. In some examples, this is the only difference and as such, aside from the differences described hereinbelow, the above discussion in respect of the second embodiment applies equally to the third embodiment.

In the third embodiment, and in the previous embodiments, the actuation member 306 is depressible by a user axially towards a distal end of the device 300. In the third embodiment, the actuation member 306 is configured to be held in a depressed position in the pre-use configuration of the device 300 (i.e. when the locking member 308 is in the locking position, prior to the locking member 308 being moved to the actuation member release position). As such, in this embodiment, the device 300 comprises an actuation member support 374 which comprises a latch 376 configured to engage with a complementary latching feature 378 provided on the actuation member 306 for holding the actuation member 306 in the depressed position when the locking member 308 is in the locking position (or when the locking member release 310 (e.g., sleeve 330) is in the first position). In this embodiment, the latching feature 378 comprises a notch or recess 378 provided in the blocking member 342 of the actuation member 306 although any other suitable latching feature may instead be used. In other embodiments, the actuation member 306 may instead comprise the latch 376 and the actuation member support 374 may instead comprise the latching feature 378. In the depressed position of the actuation member 306, the actuation member 306 is held flush or recessed within a proximal end of the locking member 308 and/or of the proximal end of the body.

In the held-depressed position of the actuation member 306, the blocking member 342 is in blocking engagement with a surface of the actuation member support 374 (or in other embodiments additionally or alternatively with a surface of the locking member 308) so as to prevent the actuation member 306 from being moved (e.g. depressed) to the actuation position. In the same way as in the second embodiment, the blocking engagement prevents the actuation member 306 from being moved (e.g. depressed) to the actuation position by a user.

In the third embodiment, the actuation member support 374 comprises an actuation member bias 380, provided in this embodiment as a compression spring although any other suitable bias may instead be used. The actuation member bias 380 is configured to bias the actuation member 306 into a raised position for being moved (e.g. depressed) by a user to the actuation position.

The actuation member 306 is rotationally coupled to the locking member 308 so as to rotate upon rotation of the locking member 308. The actuation member support 374 is rotationally decoupled from both the locking member 308 and the actuation member 306 such that rotation of the locking member 308, and thereby the actuation member 306, does not cause rotation of the actuation member support 374. In some embodiments the actuation member support 374 may be rotationally coupled to the body of the device 300, for example the actuation member support 374 may be fixed or attached to the body, either directly or indirectly, for example the actuation member support 374 may be integrally formed with the body 334.

When the user depresses the locking member release 310 against the injection site 332, the locking member release 310 is caused to move axially in a proximal direction in the same way as in the second embodiment, thereby causing the guide 326 to first move along the axially extending portion 322 of the slot 320 provided in the locking member 308. As the locking member release 310 continues to be depressed by a user, the guide 326 then enters and moves along the angled circumferentially extending portion 324, guided by the ramped surface 368 thereof. The movement of the guide 326 along the angled circumferentially extending portion 324, causes the locking member 308 to rotate, in the same way as in the second embodiment, from the locking position to the actuation member release position. Upon further depression of the locking member release 310 to the fully-depressed position, the guide 326 then enters the second axially extending portion 370 of the slot 320 corresponding with the fully-depressed position of the locking member release 310. As the locking member 308 rotates to the actuation member release position, the actuation member 306 is caused to rotate with the locking member 308 so as to cause the latch 376 to disengage from latching engagement with the latching feature 378 and, biased by the actuation member bias 380, the actuation member 306 is caused to move to a raised position in which it extends from a proximal end of the device for being moved (e.g. depressed) by a user to the actuation position.

After the actuation member 306 has moved to the raised position, the user then moves (e.g. depresses) the actuation member 306 towards the actuation position, causing the blocking member 342 to move through an aperture 372 provided in the actuation member support 374 which becomes rotationally aligned with the blocking member 342 when the actuation member 306 is rotated as the locking member 308 is rotated into the actuation member release position (but which was previously rotationally misaligned with the blocking member 342 in the locking position) so as to remove the previously blocking engagement between the blocking member 342 and the actuation member support 374. As the blocking engagement has been removed, the actuation member 306 can then be moved by the user to the actuation position to cause the needle to move from the retracted position to the exposed position for delivering a dose of medicament either by triggering a needle mechanism (such as that shown in FIGS. 2A-2G) or by the actuation member 306 acting directly on the medicament container 450 or needle and in some embodiments the movement of the actuation member 306 to the actuation position may additionally or alternative cause a dose of medicament to be dispensed through the needle, for example by triggering the release of a plunger as described in respect of FIGS. 2A-2G.

In all embodiments described herein, the device may comprise a locking member bias configured to bias the locking member 108 into its locking position or one which is configured to bias the locking member 108 into its actuation member release position. Such a bias may comprise a torsion spring or any other suitable means for biasing the locking member 108 in this way.

Furthermore, in all embodiments described herein, the slots 120; 220; and/or 320 may comprise one or more detents or projections 146 (see FIGS. 3B-3D) configured to provide a haptic or audible indication to the user upon engagement of the one or more detects or projections 128 with the guides 126; 226; and/or 326. The one or more detents or projections 146 may be arranged within the slots 120; 220; and/or 320 so as to correspond to a fully-depressed position of the locking member releases 110; 210; and/or 310 or so as to correspond to the locking members 108; 208; and/or 308 being in the actuation member release position and/or so as to correspond with the locking members 108; 208; and/or 308 being in the locking position.

LIST OF FEATURES

10—Device
11—housing
12—Cap
13—Needle sleeve
17—Needle
20—Distal region
21—Proximal region
22—Button
23—Piston
100—Medicament delivery device
104—Distal end
106—Actuation member
108—Locking member
110—Locking member release
112—Proximal end
116—Lock ring
118—Longitudinal axis
120—Slot
122—Axially extending portion
124—Circumferentially extending portion
126—Guide
128—Button
130—Sleeve
132—Injection site
134—Body
136—Locking member release bias
138—Compression spring 146—Projection
200—Medicament delivery device
206—Actuation member
208—Locking member
210—Locking member release
216—Lock ring
218—Longitudinal axis
220—Slot
222—Circumferentially extending portion
226—Guide
230—Sleeve
234—Body
236—Locking member release bias
242—Blocking member
268—Ramped surface
270—Second axially extending portion
272—Aperture
300—Medicament delivery device
306—Actuation member
308—Locking member
310—Locking member release
316—Lock ring
320—Slot
322—Axially extending portion
324—Circumferentially extending portion
326—Guide
328—Button
330—Sleeve
342—Blocking member
370—Second axially extending portion
372—Aperture
374—Actuation member support
376—Latch
378—Latching feature
380—Actuation member bias
400—Medicament delivery device
402—Needle
404—Distal end
406—Actuation member
408—Locking member
416—Lock ring
428—Button
432—Injection site
434—Body
450—Syringe
452—Plunger
458—Stop
460—Compression spring
462—Medicament container bias
464—Bias
466—Cap The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful with the devices and methods disclosed herein include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device.

Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
   a needle for injecting a medicament, the needle arranged at a distal end of the medicament delivery device, the needle being axially movable from a proximal position in which the needle is retracted within the medicament delivery device to a distal position in which a distal end of the needle extends from the distal end of the medicament delivery device for injecting the medicament;
   an actuation member configured to be movable to an actuation position to cause the needle to move from the proximal position to the distal position;
   a locking member for preventing the actuation member from moving to the actuation position, the locking member being configured to move from (i) a locking position in which the actuation member is prevented from moving to the actuation position to (ii) a release position in which the movement of the actuation member to the actuation position is allowed; and
   a locking release member configured to axially extend from the distal end of the medicament delivery device, the locking release member being axially movable towards a proximal end of the medicament delivery device from (i) a first position in which the locking member is prevented from moving to the release position to (ii) a second position in which the movement of the locking member to the release position is allowed,
   wherein the actuation member is configured to be held in a depressed position when the locking member is in the locking position or when the locking release member is in the first position.

2. The medicament delivery device of claim 1, wherein the locking member is configured to be movable from the locking position to the release position when the locking release member is in the second position.

3. The medicament delivery device of claim 1, wherein the medicament delivery device is configured such that the movement of the locking release member to the second position causes the locking member to move to the release position.

4. The medicament delivery device of claim 1, wherein the medicament delivery device is configured such that relative movement between a guide element and a slot causes the locking member to move from the locking position to the release position as the locking release member moves from the first position to the second position, the slot being angled relative to a longitudinal axis of the medicament delivery device.

5. The medicament delivery device of claim 1, wherein the medicament delivery device comprises a bias element configured to bias the locking member to the release position.

6. The medicament delivery device of claim 5, wherein the bias element comprises a spring.

7. The medicament delivery device of claim 1, wherein the locking member comprises a lock ring.

8. The medicament delivery device of claim 1, wherein the medicament delivery device comprises an axial guide configured to guide axial movement of the locking release member with respect to the locking member while limiting, restricting, or substantially preventing rotational movement of the locking release member with respect to the locking member.

9. The medicament delivery device of claim 1, wherein the actuation member is configured to be held in the depressed position when the locking release member is in the first position.

10. The medicament delivery device of claim 1, wherein the actuation member is configured to be held in the depressed position when the locking member is in the locking position.

11. The medicament delivery device of claim 1, wherein one of the locking member and the locking release member comprises a slot having an axially extending portion and a circumferentially extending portion angled with respect to the axially extending portion.

12. The medicament delivery device of claim 11, wherein the other of the locking member and the locking release member comprises a guide element configured to be slidably received within the slot so as to be slidable along and between the axially extending portion and the circumferentially extending portion.

13. The medicament delivery device of claim 12, wherein the guide element comprises a protrusion.

14. The medicament delivery device of claim 12, wherein the guide element is configured to slide along the axially extending portion of the slot as the locking release member moves to the second position.

15. The medicament delivery device of claim 12, wherein the axially extending portion is configured to limit the movement of the locking member from the locking position to the release position.

16. The medicament delivery device of claim 15, wherein the axially extending portion is configured to limit rotational movement of the locking member from the locking position to the release position.

17. The medicament delivery device of claim 12, wherein the circumferentially extending portion of the slot is angled to be substantially perpendicular to the axially extending portion.

18. The medicament delivery device of claim 12, wherein the slot comprises one or more detents or projections configured to provide a haptic or audible indication upon engagement of the one or more detents or projections with the guide element.

19. The medicament delivery device of claim 12, wherein the circumferentially extending portion of the slot is angled such that axial movement of the locking release member with respect to the locking member causes the locking member to move from the locking position to the release position.

20. The medicament delivery device of claim 12, wherein:
the axially extending portion is configured to limit the movement of the locking member from the locking position to the release position,
the circumferentially extending portion of the slot is angled to be substantially perpendicular to the axially extending portion, and
the slot comprises one or more detents or projections configured to provide a haptic or audible indication upon engagement of the one or more detents or projections with the guide element.

21. The medicament delivery device of claim 12, wherein:
the axially extending portion is configured to limit the movement of the locking member from the locking position to the release position,
the circumferentially extending portion of the slot is angled such that axial movement of the locking release member with respect to the locking member causes the locking member to move from the locking position to the release position, and
the slot comprises one or more detents or projections configured to provide a haptic or audible indication upon engagement of the one or more detents or projections with the guide element.

22. The medicament delivery device of claim 1, wherein one of the locking member or the actuation member comprises an aperture configured to align with and receive a blocking member of the other of the locking member or the actuation member when the locking member is in the release position.

23. The medicament delivery device of claim 22, wherein the medicament delivery device is configured such that when the blocking member is aligned with the aperture, the actuation member is allowed to move to the actuation position.

24. The medicament delivery device of claim 23, wherein when the locking member is not in the release position, the movement of the actuation member to the release position is limited.

25. The medicament delivery device of claim 22, wherein the aperture is defined by a slot or a recess.

26. A medicament delivery device comprising:
a housing;
a needle arranged at a distal end of the housing, the needle being axially movable between (i) a proximal needle position in which the needle is within the medicament delivery device and (ii) a distal needle position in which the distal end of the needle extends from a distal end of the housing;
a first member configured to be movable relative to the housing from a first first member position to a second first member position such that moving the first member to the second first member position causes the needle to move from the proximal needle position to the distal needle position;
a second member configured to limit the movement of the first member from the first first member position to the second first member position, the second member being configured to move from (i) a first second member position in which the movement of the first member to the second first member position is limited to (ii) a second second member position in which the movement of the first member to the second first member position is allowed; and
a third member configured to extend from the distal end of the housing, the third member being axially movable in a proximal direction relative to the housing from (i) a first third member position in which the movement of the second member to the second second member position is limited to (ii) a second third member position in which the movement of the second member to the second second member position is allowed,
wherein one of the first member or the second member comprises an aperture configured to align with and receive a blocking member of the other of the first member or the second member when the second member is in the second second member position.

27. A medicament delivery device comprising:
a housing;
a first member configured to be movable relative to the housing from a first first member position to a second first member position to cause a medicament to be dispensed from the medicament delivery device;
a second member configured to move from (i) a first second member position in which the movement of the first member to the second first member position is limited to (ii) a second second member position in which the movement of the first member to the second first member position is allowed; and
a third member configured to move in a proximal direction relative to the housing from (i) a distal position in which the movement of the second member to the second second member position is limited to (ii) a proximal position in which the movement of the second member to the second second member position is allowed,
wherein the first member is configured to be held in a depressed position when the second member is in the first second member position or when the third member is in the distal position.

28. The medicament delivery device of claim 27, wherein the movement of the second member from the first second member position to the second second member position comprises a rotation relative to the housing.

29. A method comprising:
moving a locking release member of a medicament delivery device axially towards a proximal end of the medicament delivery device from (i) a first position in which a movement of a locking member of the medicament delivery device to a release position is limited to (ii) a second position in which the movement of the locking member to the release position is allowed;

while the locking release member is in the second position, moving the locking member from (i) a locked position in which an actuation member of the medicament delivery device is held in a depressed position and a movement of the actuation member to an actuation position is limited to (ii) the release position in which the actuation member is released from being held in the depressed position and the movement of the actuation member to the actuation position is allowed; and while the locking member is in the release position, moving the actuation member to the actuation position to cause a needle to move axially from (i) a proximal position in which the needle is retracted within a distal end of the medicament delivery device to (ii) a distal position in which a distal end of the needle extends from the distal end of the medicament delivery device.

30. The method of claim 29, comprising injecting a medicament through the needle and into a patient while the needle is in the distal position.

* * * * *